United States Patent [19]

Gordon et al.

[11] Patent Number: 4,612,193

[45] Date of Patent: Sep. 16, 1986

[54] STY OINTMENT AND METHOD OF USING THE SAME

[75] Inventors: Harry W. Gordon, Wantagh; Kenneth Chung, Greenlawn, both of N.Y.

[73] Assignee: Del Laboratories, Inc., Farmingdale, N.Y.

[21] Appl. No.: 735,966

[22] Filed: May 20, 1985

Related U.S. Application Data

[63] Continuation-in-part of Ser. No. 564,716, Dec. 23, 1983, abandoned.

[51] Int. Cl.$^4$ .................. A61K 31/305; A61K 33/22; A61K 33/28
[52] U.S. Cl. .................................... 424/146; 424/148; 514/914
[58] Field of Search ................. 514/914; 424/146, 148

[56] References Cited

U.S. PATENT DOCUMENTS 1,384,863  7/1921  Shepherd ............................ 424/146
3,210,243 10/1965  Feldman ............................. 514/170
3,236,730  2/1966  Galin ................................. 424/146

OTHER PUBLICATIONS

The Extra Pharmacopocia, 1958, 24th Edition, vol. I, pp. 339, 342, 343, 881, 882, and 884 to 886.
Goodman, Cosmetic Dermatology, 5/1937, pp. 404 & 408.
Bennett, The Cosmetic Formulary, 1937, p. 95.

Primary Examiner—Dale R. Ore
Attorney, Agent, or Firm—Kirschstein, Kirschstein, Ottinger & Israel

[57] ABSTRACT

Ointment compositions for the treatment of styes and related infectious conditions of the eyelid. The ointments contain an emollient base, including white petrolatum, mineral oil and microcrystalline wax, as well as boric acid, wheat germ oil and mercuric oxide, the concentration of boric acid in the ointment is about 2-10% by weight, as is the concentration of the wheat germ oil, while the mercuric oxide is present in a concentration of about 1-1.2% by weight. The wheat germ oil enhances the anti-bacterial potency of the mercuric oxide, and the boric acid stabilizes the mercuric oxide in the presence of the wheat germ oil to prevent discoloration of the ointment.

7 Claims, No Drawings

STY OINTMENT AND METHOD OF USING THE SAME

CROSS-REFERENCE TO RELATED APPLICATION

This application is a continuation-in-part of co-pending application Ser. No. 564,716, filed Dec. 23, 1983, now abandoned.

BACKGROUND OF THE INVENTION

1. Field of the Invention

The present invention relates to compositions utilized for the treatment of styes and related inflammations of the eyelid area.

2. Description of the Prior Art

A sty, technically known as a hordeolum, is a furuncular inflammation of the connective tissue of the eyelid near a hair follicle. Styes are generally caused by bacterial infections of the sebaceous or marginal glands of the eyelid and are one type of blepharitic infection, i.e. infections causing inflammation of the eyelids. Styes and other blepharitic infections are generally responsive to topical antibacterial agents, and a variety of such agents have been incorporated into topical preparations to be applied to the eyelid for the treatment of such infections.

Among the preparations commonly used for the treatment of styes and other infections of a similar nature, are ointments containing, for example, a carrier such as petrolatum, mineral oil or lanolin, an astringent such as zinc sulfate, and a bactericidal agent, frequently a mercury salt such as mercuric iodide or mercuric oxide. One representative commercially available sty ointment contains about 1% yellow mercuric oxide in an ointment base consisting primarily of petrolatum and mineral oil.

Many of the prior art sty ointments as well as other topical germicidal ointments also contain a small quantity (on the order of a few percent by weight) of boric acid, which serves to stabilize the mercuric oxide against color/chemical deterioration. Examples of the use of boric acid and related compounds as stabilizers in antiseptic ointments are disclosed in U.S. Pat. Nos. 1,493,564 and 372,852.

Although the mercuric oxide or other mercury-compound containing petrolatum-type ointments have been effective in the absence of boric acid for the treatment of styes and related blepharitic infections, these preparations have shelf lives of less than about six months because the mercuric oxide active ingredient thereafter tends to decompose and discolor, turning a dark brown shade. This gives the prior art ointments an aesthetically displeasing appearance and discourage patient use of the same, making it commercially undesirable. Such discouragement is particularly detrimental in view of the fact that most mercuric oxide-containing sty ointments are marketed over the counter and do not require a physician's prescription; hence, the consumer is completely free to choose which ointment to use if any, and an ointment which discolors within a few months after manufacture is not attractive to the consuming public, even if medically effective.

Another drawback of prior art sty ointments, even those containing boric acid as a stabilizer, is that the preparations experience a reduction in their germicidal potency, and hence, their therapeutic efficacy, after about six months, particularly once the ointment containers have been opened. Moreover, no prior art sty ointment contains an ingredient or ingredients to enhance the bactericidal potency of the preparation and thus delay the time when the level of its therapeutic efficacy becomes unacceptable. To the present date, no preparation effective for the treatment of styes and similar infections of the eyelid has been developed which has a shelf life of more than about six months, both from the point of view of maintaining its original color and aesthetic appearance and from the point of view of substantially maintaining its germicidal potency, and yet contains only ingredients safe enough for use in an over the counter preparation purchased by self-medicating consumers.

SUMMARY OF THE INVENTION

Objects of the Invention

It is an object of the present invention to provide compositions for use in the treatment of styes, blepharitis and related inflammatory conditions of the eyelid that are safe, effective, and have a long shelf life.

An additional object of the present invention is to provide compositions as described above which contain mercuric oxide and yet resist discoloration for long periods of time.

A further object of the present invention is to provide compositions as described above which maintain a high level of therapeutic efficacy for substantial periods of time.

Still another object of the present invention is to provide compositions as described above which are safe enough for use by self-medicating patients and yet are effective in combatting the infection and inflammation associated with styes and related conditions of the eyelid.

Brief Description of the Invention

In keeping with these objects and others which will become apparent hereinafter, the present invention resides, briefly stated, in compositions and a method for the treatment of styes and related blepharitic conditions in which the compositions comprise about 0-10% microcrystalline wax NF, 10-60% mineral oil USP, 1-1.2% yellow mercuric oxide, 2-10% boric acid NF, 2-10% wheat germ oil, and white petrolatum USP q.s. to 100% in an amount sufficient to give the desired viscosity and appearance to the composition. The mineral oil is considered to be the essential vehicle for the mercuric oxide which is the active bactericide of the composition. The white petrolatum and the microcrystalline wax act as conventional consistency modifiers for the composition to insure that the resultant ointment is a smooth emolient viscous enough to adhere to the eyelid whereby to enable the mercuric oxide bacteriologically active ingredient to exert its anti-infective properties, but not so viscous as to be unspreadable by the user. The amount of petrolatum and wax added must be carefully controlled to avoid making the ointment so viscous, moreover, that it causes blurred vision, for example, by creating an oil coating on the cornea which remains in place for too extended a period of time.

Microcrystalline wax has been shown to be very useful in forming stable preparations in the form of ointments or gels and to enhance the spreadability of such preparations. An example of an emollient gel containing microcrystalline wax is disclosed in U.S. Pat. No. 3,210,248.

The key point of novelty in the compositions of the present invention is the inclusion of a small amount of wheat germ oil which acts as a homogenizer for the remaining ingredients in the preparation and potentiates, i.e. enhances, the activity of the mercuric oxide active ingredient. The addition of wheat germ oil has been found to noticeably enhance the antimicrobial activity of the mercuric oxide containing ointment and to maintain the therapeutic efficacy of the preparation for a much loner period of time than was achieved with prior sty ointments.

Wheat germ oil is obtained by hydraulic expression or solvent extraction of wheat germ and contains roughly 70% unsaturated fatty acids. Commercially available wheat germ oils are suitable for use in the subject compositions, such as, by way of example, VIOBIN (Viobin Corp., Monticello, Illinois) and VITINC (Vitamins, Inc., Chicago, Illinois) wheat germ oil which contain an almost negligible amount, e.g. from about 0.1 to about 0.2% by weight of Vitamin E.

In the compositions of the invention, the boric acid acts as a stabilizer for the mercuric oxide and wheat germ oil, i.e. it inhibits the chemical deterioration of these materials, and is effective in preventing discoloration and loss of antibacterial potency of the mercury constituent for substantially longer than is possible in preparations containing only mercuric oxide with no wheat germ oil.

Comparative testing has demonstrated that the bactericidal efficacy of compositions containing wheat germ oil in addition to mercuric oxide is substantially greater than compositions containing mercuric oxide alone. Such testing included bacteriological evaluations which demonstrated the increased potency of preparations containing wheat germ oil in comparison with those that did not.

In general, the compositions of the present invention are formulated so as to be of pleasant appearance, sufficiently viscous to adhere to the eyelid, but not so viscous as to cause blurring of vision or other discomfort, easily spreadable, capable of a high degree of color stability and possessing long shelf life, both in terms of discoloration and in terms of loss of therapeutic potency.

DETAILED DESCRIPTION OF THE INVENTION

The compositions of the present invention are, essentially, ointments for topical treatment of styes, blepharitis and related infections or inflammations of the eyelids.

These compositions comprise, by weight, 10-60% mineral oil, 0-10% microcrystalline wax, 2-10% wheat germ oil, 2-10% boric acid, 1-1.2% yellow mercuric oxide USP/NF, and white petrolatum USP q.s. to 100% by weight of the composition in an amount sufficient to yield a desired viscosity and appearance to the composition. The preferred weight ranges for the subject compositions are 3-7% for the wheat germ oil and 2-5% for the boric acid, with the weight ratio of the wheat germ oil to the boric acid being optimally between 1:1 and 2:1.

The mineral oil constituent of the ointments preferably has a specific gravity of 0.830-0.905 at 25° C. and serves as the diluent and vehicle for the mercuric oxide. The mineral oil, which can be, by way of example, mineral oil USP or white mineral oil N.F. ("Blandol"), is not viscous enough by itself to serve as a base for an ointment suitable for topical application to the eyelid. But when the mineral oil is combined with the white petrolatum and the microcrystalline wax, a smooth emollient ointment base of uniform consistency is obtained, with a viscosity of from about 88,000 to 143,600 cps. While this viscosity is somewhat reduced by the addition of wheat germ oil, the addition of the boric acid and mercuric oxide in powdered form restores the viscosity of the ointment to the range of about 82,000 to about 140,000 cps.

Microcrystalline wax is a mixture of straight-chain, branched chain and cyclic hydrocarbons, obtained by solvent fractionation of the bottom fraction of petroleum by suitable dewaxing means. Waxes suitable for use in the subject compositions are, e.g., microcrystalline wax N.F. or one of the "Multiwax" waxes produced by Witco Chemical Company.

As discussed previously and as has been disclosed in the prior art, the petrolatum acts as a consistency modifier for the mineral oil, as does the microcrystalline wax. The wax helps give the ointment firmness while also adding the property of easy and uniform spreadability, which is important in an ointment to be applied to the eyelid where it is desirable to achieve a thin, uniform coating of the medication for maximum benefit.

The novelty of the present compositions resides chiefly in the use of both wheat germ oil and boric acid together with the mercuric oxide active ingredient. It has been found that wheat germ oil potentiates, i.e. enhances, the bactericidal activity of mercuric oxide in an ointment base of the type utilized in the subject compositions, rendering these compositions of heightened therapeutic potency in the treatment of styes and related inflammatory conditions of the eyelid. Moreover, the boric acid component of the compositions stabilizes the mercuric oxide in the presence of the wheat germ oil and acts to retard discoloration of the mercuric oxide while helping sustain its antibacterial efficacy for long periods of time. Hence, while prior art sty ointments containing mercuric oxide have a shelf life of only about six months before discoloration of the product begins, the compositions of the present invention can retain their original light color with little change for two years and more. In addition, the stability of the mercuric oxide in the instant preparations is so great that these preparations can be effectively utilized even after a shelf life in excess of two years.

The compositions of the present invention can be conveniently produced on a commercial scale by mixing the petrolatum, mineral oil and microcrystalline wax in a sterile tank while heating to approximately 85° C. The mixture is then filtered into a second mixing tank where it is cooled to room temperature. Subsequently, filtered wheat germ oil is added to the cooled ointment base and mixed therewith until a uniform consistency is achieved.

The boric acid and yellow mercuric oxide, both in powdered form, are presterilized by dry heating at approximately 120° C. and then added to the ointment base with the wheat germ oil, with further mixing being employed. Finally, the ointment is roller milled until a smooth and uniform product is obtained.

The following are illustrative examples of the preparation of sty ointment compositions in accordance with the present invention, as well as experimental data domonstrating the enhanced bactericidal efficacy of these compositions attributable to the presence of the wheat germ oil and the high stability of the mercuric oxide active ingredient and the wheat germ oil as a result of the boric acid present in the formulation. These examples are not intended, however, to limit or restrict the scope of the invention in any way and should not be construed as identifying specific materials, parameters or ranges which must be utilized exclusively in order to make, use, test or analyze the compositions of the present invention.

EXAMPLE I

Preparation of a Sty Ointment Composition 54.5 g. of white petrolatum USP, 31.9 g. of mineral oil USP and 5.0 g. of microcrystalline wax (Multiwax W445 —Witco Chemical Co.) were charged into a sterile reaction vessel with an agitator. The mixture was agitated while being gradually heated to 85° C. After about 30 minutes, a homogeneous mixture was achieved which was then filtered through a 0.22 micron membrane filtering unit into a second mixing vessel. The second vessel was agitated for about 45 minutes as the mixture cooled to room temperature. 5.0 g. of wheat germ oil at room temperature was filtered through a 0.22 micron filtering unit and added to the petrolatum, oil and wax mixture in the mixing vessel. Agitation of the mixture was continued for about 15 to 30 minutes until the mixture was again uniform. 2.5 g. of impalpable boric acid (having a particle size of under 25 microns) and 1.1 g. of yellow mercuric oxide were presterilized by dry heating at 120° C. for 24 hours and then added to the mixing vessel containing the wheat germ oil and other ointment base ingredients. Mixing was continued for an additional 15 to 20 minutes until an ointment of homogeneous appearance was achieved. This ointment was passed through a triple-roller mill twice at a setting close enough to yield a particle size of 15-20 microns. After the addition of the boric acid and mercuric oxide, the specific gravity of the resultant ointment was about 0.8351-0.8799, while the viscosity was in the range of 82,000-140,000 cps.

The total weight of the ointment product was approximately 100 g., of which the ingredients constituted the following weight percentages:

| | |
|---|---|
| White petrolatum | 54.5% |
| Mineral Oil | 31.9% |
| Microcrystalline wax | 5.0% |
| Wheat germ oil | 5.0% |
| Boric Acid | 2.5% |
| Yellow mercuric oxide | 1.1% |

The wheat germ oil utilized was VIOBIN wheat germ oil (Viobin Corp., Monticello, Illinois), and contained 69.0% unsaturated fatty acids (46.9% linoleic, 15.7% oleic, 5.9% linolenic and 0.2% arachidonic), 15.5% saturated fatty acids (primarily palmitic), 8.0% free fatty acids, 6.0% phosphatides and 4.7% unsaponifiables (predominantly sterols). The vitamin E content of the wheat germ oil was under 0.2% by weight.

Relative Antibacterial Activity of Compositions Containing Varying Concentrations of Wheat Germ Oil Eleven ointment compositions were prepared in accordance wih the method set forth in Example 1, each composition being designated with a capital letter from A to K. The ingredients of these 11 preparations by weight percentages were as follows:

TABLE I

| Ingredients | A | B | C | D | E | F | G | H | I | J | K |
|---|---|---|---|---|---|---|---|---|---|---|---|
| Ointment base (Blandol, white petrolatum USP, Multiwax W445) | 95.9 | 94.9 | 93.9 | 92.9 | 91.9 | 90.9 | 89.9 | 88.9 | 87.9 | 86.9 | 85.9 |
| Boric acid | 3.0 | 3.0 | 3.0 | 3.0 | 3.0 | 3.0 | 3.0 | 3.0 | 3.0 | 3.0 | 3.0 |
| Yellow mercuric oxide USP/NF | 1.1 | 1.1 | 1.1 | 1.1 | 1.1 | 1.1 | 1.1 | 1.1 | 1.1 | 1.1 | 1.1 |
| Wheat germ oil | 0.0 | 1.0 | 2.0 | 3.0 | 4.0 | 5.0 | 6.0 | 7.0 | 8.0 | 9.0 | 10.0 |

The eleven preparations were thus of identical composition except for the concerntration of wheat germ oil therein with said concentration increasing from 0% in preparation A to 10% in preparation K.

A bacterial culture, Staph aureus ATCC #6538 (a strain of the type implicated in styes and related infections), was grown on trypticase soy agar for 24 hours. The culture was identified by characteristic growth on Mannitol Salt agar and a positive coagulase test. Four colonies were taken with a swab and inoculated into trypticase soy broth, which was incubated at 35° C. for 4 hours. The broth inoculum was adjusted with trypticase soy broth on a Spectronic 20 at 600 nm to 80% transmittance. A sterile swab was then dipped into the prepared inoculum and rotated gainst the upper wall of the tube to remove excess fluid. The swabs were streaked across 150 mm petri dishes filled with 75 ml. of sterile BB1 Mullers Hinton Agar. Each plate was streaked 3 times, with the plates being rotated 60° between streakings.

The Bauer-Kirby technique was used for antimicrobial susceptibility testing. The test was modified by cutting sample wells in the agar having a diameter of 7 mm, using a #4 cork borer. Approximately 0.15 ml. of each of fresh preparations A through K was added with a syringe to a different one of the sampling wells in the agar. The dishes were incubated without inverting for 18 hours at 35° C.

The results of the anti-microbial test were determined by the diameter of the zones of inhibition around each of the sample wells. The results of the test were as follows:

TABLE II

| | A | B | C | D | E | F | G | H | I | J | K |
|---|---|---|---|---|---|---|---|---|---|---|---|
| Concentration | 0.0 | 1.0 | 2.0 | 3.0 | 4.0 | 5.0 | 6.0 | 7.0 | 8.0 | 9.0 | 10.0 |

TABLE II-continued

| | A | B | C | D | E | F | G | H | I | J | K |
|---|---|---|---|---|---|---|---|---|---|---|---|
| of wheat germ oil | | | | | | | | | | | |
| Zone Size (mm) | 12.2 | 14.7 | 10.8 | 14.15 | 14.15 | 14.65 | 14.9 | 15.3 | 15.1 | 16.0 | 16.3 |

Hence, a faily consistent trend showing increased antimicrobial activity with increased concentration of wheat germ oil was established.

Relative Antibacterial Activity of Compositions Containing Varying Concentrations of Boric Acid The test described above was repeated with six more fresh ointment preparations, designated L through Q, each prepared in accordance with the procedure set forth above. All of the ointments contained 10% wheat germ oil, but had concentrations of boric acid varying from 0-5%.

The results of the antibacterial test on preparations L through Q were as follows:

TABLE III

| | L | M | N | O | P | Q |
|---|---|---|---|---|---|---|
| Concentration of boric acid | 5.0 | 4.0 | 3.0 | 2.0 | 1.0 | 0.0 |
| Zone size (mm) | 20.3 | 20.3 | 20.3 | 20.6 | 20.6 | 20.0 |

Hence, there was no significant variation in the antimicrobial potency of the tested ointment preparations despite variations in the concentration of boric acid.

The test data shown in Table II and Table III demonstrate that increasing the concerntration of the wheat germ oil component of the ointments of the present invention considerably enhances their antibacterial activity in comparison with compositions containing little or no wheat germ oil, while varying the concentration of boric acid, which was also used in prior art sty ointment compositions, does not improve antibacterial activity.

Stability Study on Compositions With Varying Concentrations of Boric Acid

Five ointments were prepared in accordance with the foregoing procedures with the concentration of boric acid in those preparations varying from 0 to 5%. The stability of the preparations (stored in both glass and high density polyethylene containers), each containing 10% wheat germ oil and 1.1% yellow mercuric oxide, was determined after a period of two months at 48° C. The following stability percentages, determined by analysis, represent the relative amount of mercuric oxide which was not reduced to the visually unattractive mercurous form.

The results of this stability test were as follows:

TABLE IV

| Concentration of Boric Acid | 0% | 1% | 2% | 3% | 4% | 5% |
|---|---|---|---|---|---|---|
| % Stability of Mercuric Oxide | 2% | 20% | 92% | 95% | 98% | 100% |

This test evidenced the ability of boric acid, in concentrations as low as 5%, to efficiently stabilize the mercuric oxide anti-microbial component of the compositions of the present invention in the presence of a 10% concentration of wheat germ oil.

The ointment compositions of the invention are utilized by direct application of a thin coating to the eyelids and particularly to the area or areas of inflammation. The preparations have been found safe for topical ophthalmic use and have not been found to cause any degree of sensitization, irritation or other untoward side effect.

The advantages provided by the novel compositions are numerous. These novel anti-sty ointments are highly stable in terms of coloration and therapeutic efficacy for long periods of time, and have enhanced antibacterial activity of the type essential in combatting the infections, e.g. of styes and blepharitis. The unique combination of mercuric oxide, wheat germ oil and boric acid in an emollient ointment base yields a product which is safe enough for use by self-medicating patients and for over-the-counter sale while at the same time being more effective than currently available products sold for the same purpose.

It will thus be seen that there are provided compositions which achieve the various objects of the invention and which are well adapted to meet the conditions of practical use. As various possible embodiments might be made of the above invention and as various changes might be made in the embodiments above set forth, it is to be understood that all matter herein described is to be interpreted as illustrative and not in a limiting sense.

What is claimed as new and desired to be protected by Letters Patent is set forth in the appended claims.

We claim:

1. In an ointment composition for the treatment of styes, comprising an emollient ointment base and about 1-1.2% yellow mercuric oxide by weight of the composition, wherein the improvement comprises increasing the color stability and enhancing the therapeutic efficacy of the composition by the addition of: about 2-10% wheat germ oil by weight of the composition to enhance the antimicrobial activity of the yellow mercuric oxide and about 2-10% boric acid by weight of the composition to stabilize the yellow mercuric oxide in the presence of the wheat germ oil and to retard discoloration of the yellow mercuric oxide while helping to sustain its antibacterial activity for long periods of time so as to obtain an effective life for the composition in excess of two years.

2. A composition according to claim 1, which has a viscosity in the range of 88,000 to about 140,000 cps.

3. A composition according to claim 1, which has specific gravity of from 0.8351 to 0.8799.

4. A composition according to claim 1, which essentially consists of

| | Percentage By Weight of Composition |
|---|---|
| Mineral Oil | 10-60 |
| Microcrystalline wax | 0-10 |
| Boric Acid | 2-10 |
| Yellow Mercuric Oxide | 1-1.2 |
| Wheat Germ Oil | 2-10 |

White Petrolatum q.s. to 100% to give desired viscosity and appearance.

5. A composition according to claim 4, wherein the wheat germ oil constitutes 3-7% by weight of the composition by weight and the boric acid constitutes 2-5% of the composition by weight with the weight ratio of the wheat germ oil to the boric acid being in the range 1:1 to 2:1.

6. A composition according to claim 5, which essentially consists of

| | Percentage By Weight of Composition |
|---|---|
| White petrolatum | 54.5 |
| Mineral oil | 31.9 |
| Microcrystalline wax | 5.0 |
| Boric Acid | 2.5 |
| Yellow mercuric oxide | 1.1 |
| Wheat germ oil | 5.0 |

7. A method of treating styes comprising directly applying to the eyelids in the area of inflammation a thin coating of the composition of claim 1.

* * * * *